(12) United States Patent
Al-Ali et al.

(10) Patent No.: US 8,840,549 B2
(45) Date of Patent: Sep. 23, 2014

(54) MODULAR PATIENT MONITOR

(75) Inventors: Ammar Al-Ali, San Juan Capistrano, CA (US); Paul Jansen, San Clemente, CA (US); Massi Joe Kiani, Laguna Niguel, CA (US); Anand Sampath, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 11/903,746

(22) Filed: Sep. 24, 2007

(65) Prior Publication Data

US 2008/0108884 A1 May 8, 2008

Related U.S. Application Data

(60) Provisional application No. 60/846,471, filed on Sep. 22, 2006.

(51) Int. Cl.
*A61B 5/00* (2006.01)
*A61B 5/1455* (2006.01)

(52) U.S. Cl.
CPC .............. *A61B 5/0002* (2013.01); *A61B 5/1455* (2013.01); *A61B 2560/0456* (2013.01); *A61B 5/7445* (2013.01)
USPC .......................................................... 600/301

(58) Field of Classification Search
None
See application file for complete search history.

(56) References Cited

U.S. PATENT DOCUMENTS

| | | | |
|---|---|---|---|
| 3,978,849 A | 9/1976 | Geneen | |
| 4,108,166 A | 8/1978 | Schmid | |
| 4,231,354 A | 11/1980 | Kurtz et al. | |
| 4,589,415 A | 5/1986 | Haaga | |
| 4,662,378 A | 5/1987 | Thomis | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |

(Continued)

FOREIGN PATENT DOCUMENTS

| | | |
|---|---|---|
| EP | 2 335 569 A2 | 6/2011 |
| WO | WO/2004/056266 | 7/2004 |
| WO | WO/2004/059551 | 7/2004 |

OTHER PUBLICATIONS

Extended European Search Report for European Application No. 10195398.2 dated Jul. 5, 2012.

(Continued)

*Primary Examiner* — William Thomson
*Assistant Examiner* — Bobby Soriano
(74) *Attorney, Agent, or Firm* — Knobbe, Martens, Olson & Bear, LLP

(57) ABSTRACT

A modular patient monitor has a docking station configured to accept a handheld monitor. The docking station has standalone patient monitoring functionality with respect to a first set of parameters. At least some of the first parameter set are displayed simultaneously on a full-sized screen integrated with the docking station. The handheld monitor also has standalone patient monitoring functionality with respect to a second set of parameters. At least some of the second set of parameters are displayed simultaneously on a handheld-sized screen integrated with the handheld monitor. The docking station has a port configured to accept the handheld monitor. While the handheld monitor is docket in the port, the docking station functionally combines the first set of parameters and the second set of parameters, and at least some of the combined first and second sets of parameters are displayed simultaneously on the full-sized screen.

15 Claims, 17 Drawing Sheets

(56) References Cited

U.S. PATENT DOCUMENTS

| | | | |
|---|---|---|---|
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,318,037 A | 6/1994 | Evans et al. |
| 5,319,355 A | 6/1994 | Russek |
| 5,333,106 A | 7/1994 | Lanpher et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,375,599 A | 12/1994 | Shimizu |
| 5,377,676 A | 1/1995 | Vari et al. |
| 5,400,794 A | 3/1995 | Gorman |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,579,001 A | 11/1996 | Dempsey et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,685,299 A | 11/1997 | Diab et al. |
| 5,724,983 A | 3/1998 | Selker et al. |
| 5,725,308 A | 3/1998 | Smith et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,822,546 A | 10/1998 | George |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,931,160 A | 8/1999 | Gilmore et al. |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,106,463 A | 8/2000 | Wilk |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,183,417 B1 * | 2/2001 | Geheb et al. ............... 600/301 |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 * | 4/2001 | Maschke et al. ............ 600/301 |
| 6,224,553 B1 | 5/2001 | Nevo |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,524,240 B1 * | 2/2003 | Thede ........................ 600/300 |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 * | 11/2003 | Causey et al. ............... 600/300 |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |

(56) References Cited

U.S. PATENT DOCUMENTS

| | | |
|---|---|---|
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,751,492 B2 | 6/2004 | Ben-Haim |
| 6,760,607 B2 | 7/2004 | Al-Ali |
| 6,770,028 B1 | 8/2004 | Ali et al. |
| 6,771,994 B2 | 8/2004 | Kiani et al. |
| 6,790,178 B1 * | 9/2004 | Mault et al. ............. 600/300 |
| 6,792,300 B1 | 9/2004 | Diab et al. |
| 6,795,724 B2 | 9/2004 | Hogan |
| 6,807,050 B1 * | 10/2004 | Whitehorn et al. ...... 361/679.23 |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,898,452 B2 | 5/2005 | Al-Ali et al. |
| 6,915,149 B2 | 7/2005 | Ben-Haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,980,419 B2 * | 12/2005 | Smith et al. ............. 361/681 |
| 6,983,179 B2 | 1/2006 | Ben-Haim |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,063,666 B2 | 6/2006 | Weng et al. |
| 7,067,893 B2 | 6/2006 | Mills et al. |
| 7,079,035 B2 | 7/2006 | Bock et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 * | 3/2007 | DeVries et al. .......... 128/204.21 |
| 7,190,261 B2 | 3/2007 | Al-Ali |
| 7,208,119 B1 * | 4/2007 | Kurtock et al. ................. 422/61 |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,313,423 B2 * | 12/2007 | Griffin et al. ............... 455/575.2 |
| 7,314,446 B2 | 1/2008 | Byrd et al. |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,462,151 B2 | 12/2008 | Childre et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |

(56) References Cited

U.S. PATENT DOCUMENTS

| | | |
|---|---|---|
| 7,530,949 B2 | 5/2009 | Al Ali et al. |
| 7,530,955 B2 | 5/2009 | Diab et al. |
| 7,549,961 B1 | 6/2009 | Hwang |
| 7,551,717 B2 | 6/2009 | Tome et al. |
| 7,563,110 B2 | 7/2009 | Al-Ali et al. |
| 7,577,475 B2 | 8/2009 | Cosentino et al. |
| 7,596,398 B2 | 9/2009 | Al-Ali et al. |
| 7,597,665 B2 | 10/2009 | Wilk et al. |
| 7,612,999 B2 * | 11/2009 | Clark et al. ............... 361/679.4 |
| 7,618,375 B2 | 11/2009 | Flaherty |
| D606,659 S | 12/2009 | Kiani et al. |
| 7,639,145 B2 | 12/2009 | Lawson et al. |
| 7,647,083 B2 | 1/2010 | Al-Ali et al. |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| RE41,317 E | 5/2010 | Parker |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,820,184 B2 | 10/2010 | Strizker et al. |
| 7,822,452 B2 | 10/2010 | Schurman et al. |
| RE41,912 E | 11/2010 | Parker |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-ali et al. |
| 8,190,227 B2 | 5/2012 | Diab et al. |
| 8,203,438 B2 | 6/2012 | Kiani et al. |
| 8,206,312 B2 | 6/2012 | Farquhar |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,249,815 B2 | 8/2012 | Taylor |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,294,716 B2 | 10/2012 | Lord et al. |
| 8,311,747 B2 | 11/2012 | Taylor |
| 8,311,748 B2 | 11/2012 | Taylor et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,360,936 B2 | 1/2013 | DiBenedetto et al. |
| 2001/0031922 A1 | 10/2001 | Weng et al. |
| 2002/0052311 A1 | 5/2002 | Solomon et al. |
| 2002/0140675 A1 | 10/2002 | Ali et al. |
| 2002/0198445 A1 | 12/2002 | Dominguez et al. |
| 2003/0027326 A1 * | 2/2003 | Ulmsten et al. ............ 435/287.1 |
| 2004/0013647 A1 | 1/2004 | Solomon et al. |
| 2004/0073095 A1 * | 4/2004 | Causey et al. ................ 600/300 |
| 2004/0090742 A1 | 5/2004 | Son et al. |
| 2004/0122787 A1 | 6/2004 | Avinash et al. |
| 2004/0126007 A1 | 7/2004 | Ziel et al. |
| 2004/0147818 A1 * | 7/2004 | Levy et al. ................... 600/300 |
| 2004/0152957 A1 * | 8/2004 | Stivoric et al. ............... 600/300 |
| 2004/0179332 A1 | 9/2004 | Smith et al. |
| 2004/0186357 A1 * | 9/2004 | Soderberg et al. ........... 600/300 |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0254431 A1 | 12/2004 | Shehada et al. |
| 2004/0254432 A1 | 12/2004 | Shehada et al. |
| 2005/0020918 A1 | 1/2005 | Wilk et al. |
| 2005/0038332 A1 * | 2/2005 | Saidara et al. ............... 600/347 |
| 2005/0038680 A1 * | 2/2005 | McMahon ........................ 705/3 |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0113653 A1 * | 5/2005 | Fox et al. .................... 600/300 |
| 2005/0164933 A1 | 7/2005 | Tymianski et al. |
| 2005/0191294 A1 | 9/2005 | Arap et al. |

(56) References Cited

U.S. PATENT DOCUMENTS

| | | |
|---|---|---|
| 2005/0277872 A1 | 12/2005 | Colby et al. |
| 2006/0058647 A1 | 3/2006 | Strommer et al. |
| 2006/0089543 A1 | 4/2006 | Kim et al. |
| 2006/0094936 A1* | 5/2006 | Russ .............................. 600/300 |
| 2006/0149393 A1 | 7/2006 | Calderon |
| 2006/0155175 A1 | 7/2006 | Ogino et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1* | 10/2006 | Kim et al. .......................... 705/2 |
| 2006/0235300 A1 | 10/2006 | Weng et al. |
| 2006/0253042 A1 | 11/2006 | Stahmann et al. |
| 2007/0000490 A1* | 1/2007 | DeVries et al. .......... 128/204.21 |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1* | 3/2007 | Clark et al. ................... 600/300 |
| 2007/0055544 A1 | 3/2007 | Jung et al. |
| 2007/0060798 A1 | 3/2007 | Krupnik et al. |
| 2007/0088406 A1 | 4/2007 | Bennett et al. |
| 2007/0118399 A1 | 5/2007 | Avinash et al. |
| 2007/0140475 A1* | 6/2007 | Kurtock et al. ............ 379/433.01 |
| 2007/0156033 A1* | 7/2007 | Causey et al. ................. 600/300 |
| 2007/0163589 A1* | 7/2007 | DeVries et al. .......... 128/204.21 |
| 2007/0185390 A1* | 8/2007 | Perkins et al. ................. 600/300 |
| 2007/0232941 A1 | 10/2007 | Rabinovich |
| 2007/0244724 A1 | 10/2007 | Pendergast et al. |
| 2007/0255114 A1* | 11/2007 | Ackermann et al. .......... 600/300 |
| 2007/0255116 A1* | 11/2007 | Mehta et al. ................... 600/300 |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0053438 A1* | 3/2008 | DeVries et al. .......... 128/204.21 |
| 2008/0058657 A1 | 3/2008 | Schwartz et al. |
| 2008/0090626 A1* | 4/2008 | Griffin et al. ................. 455/575.1 |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1* | 5/2008 | Niemiec et al. ................ 206/528 |
| 2008/0108884 A1 | 5/2008 | Kiani |
| 2008/0119412 A1 | 5/2008 | Tymianski et al. |
| 2008/0138278 A1 | 6/2008 | Scherz et al. |
| 2008/0171919 A1* | 7/2008 | Stivoric et al. ................. 600/301 |
| 2008/0208912 A1 | 8/2008 | Garibaldi |
| 2008/0221396 A1* | 9/2008 | Garces et al. ................. 600/300 |
| 2008/0228077 A1 | 9/2008 | Wilk et al. |
| 2008/0275309 A1* | 11/2008 | Stivoric et al. ................. 600/300 |
| 2008/0281167 A1* | 11/2008 | Soderberg et al. ............ 600/300 |
| 2008/0281168 A1* | 11/2008 | Gibson et al. ................. 600/301 |
| 2008/0281181 A1 | 11/2008 | Manzione et al. |
| 2008/0287751 A1* | 11/2008 | Stivoric et al. ................. 600/301 |
| 2008/0292172 A1 | 11/2008 | Assmann et al. |
| 2008/0319275 A1 | 12/2008 | Chiu et al. |
| 2008/0319354 A1* | 12/2008 | Bell et al. ...................... 600/595 |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0264778 A1 | 10/2009 | Markowitz et al. |
| 2009/0281462 A1 | 11/2009 | Heliot et al. |
| 2010/0030094 A1 | 2/2010 | Lundback |
| 2010/0036209 A1 | 2/2010 | Ferren et al. |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0261979 A1 | 10/2010 | Kiani |
| 2010/0298659 A1 | 11/2010 | Mccombie et al. |
| 2010/0298661 A1 | 11/2010 | Mccombie et al. |
| 2010/0305412 A1 | 12/2010 | Darrah et al. |
| 2010/0312103 A1 | 12/2010 | Gorek et al. |
| 2010/0317951 A1 | 12/2010 | Rutkowski et al. |
| 2011/0021930 A1 | 1/2011 | Mazzeo et al. |
| 2011/0028809 A1 | 2/2011 | Goodman |
| 2011/0046495 A1 | 2/2011 | Osypka |
| 2011/0080294 A1 | 4/2011 | Tanishima et al. |
| 2011/0087084 A1 | 4/2011 | Jeong et al. |
| 2011/0087117 A1 | 4/2011 | Tremper et al. |
| 2011/0098583 A1 | 4/2011 | Pandia et al. |
| 2011/0118573 A1 | 5/2011 | Mckenna |
| 2011/0184252 A1 | 7/2011 | Archer et al. |
| 2011/0184253 A1 | 7/2011 | Archer et al. |
| 2011/0208018 A1 | 8/2011 | Kiani |
| 2011/0208073 A1 | 8/2011 | Matsukawa et al. |
| 2011/0212090 A1 | 9/2011 | Pedersen et al. |
| 2011/0257544 A1 | 10/2011 | Kaasinen et al. |
| 2011/0295094 A1 | 12/2011 | Doyle et al. |
| 2012/0004579 A1 | 1/2012 | Luo et al. |
| 2012/0059230 A1 | 3/2012 | Teller et al. |
| 2012/0071771 A1 | 3/2012 | Behar |
| 2012/0101353 A1 | 4/2012 | Reggiardo et al. |
| 2012/0123799 A1 | 5/2012 | Nolen et al. |
| 2012/0136221 A1 | 5/2012 | Killen et al. |
| 2012/0197619 A1 | 8/2012 | Namer Yelin et al. |
| 2012/0226160 A1 | 9/2012 | Kudoh |
| 2012/0239434 A1 | 9/2012 | Breslow et al. |
| 2012/0282583 A1 | 11/2012 | Thaler et al. |
| 2012/0294801 A1 | 11/2012 | Scherz et al. |
| 2013/0006131 A1 | 1/2013 | Narayan et al. |
| 2013/0006151 A1 | 1/2013 | Main et al. |
| 2013/0035603 A1 | 2/2013 | Jarausch et al. |

OTHER PUBLICATIONS

PCT International Search Report & Written Opinion, App. No. PCT/US2012/060109, App. Date: Dec. 10, 2012, in 17 pages.

Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.

* cited by examiner

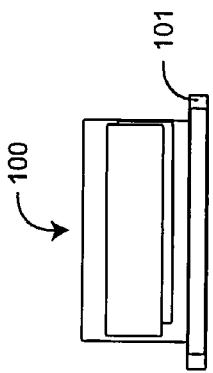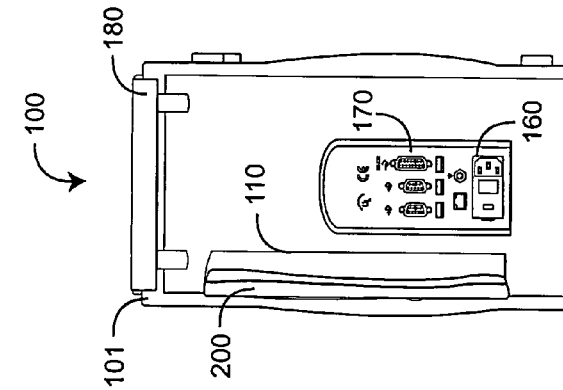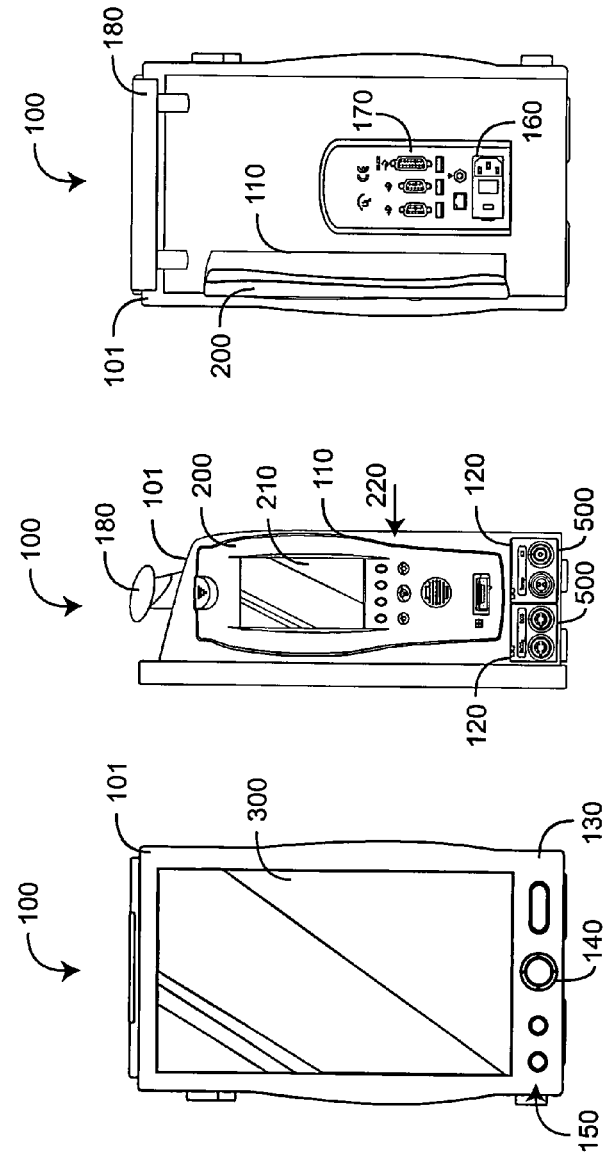

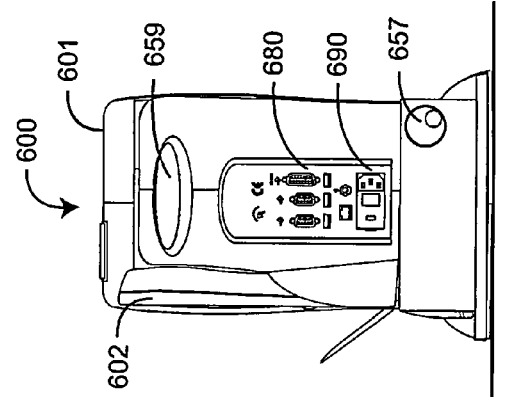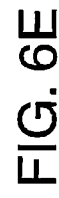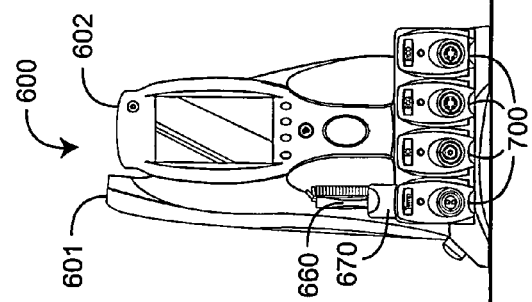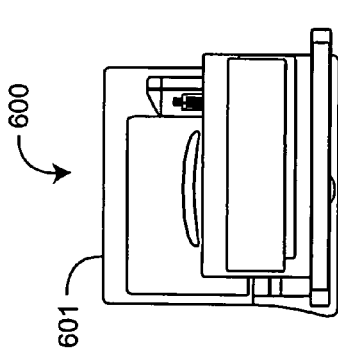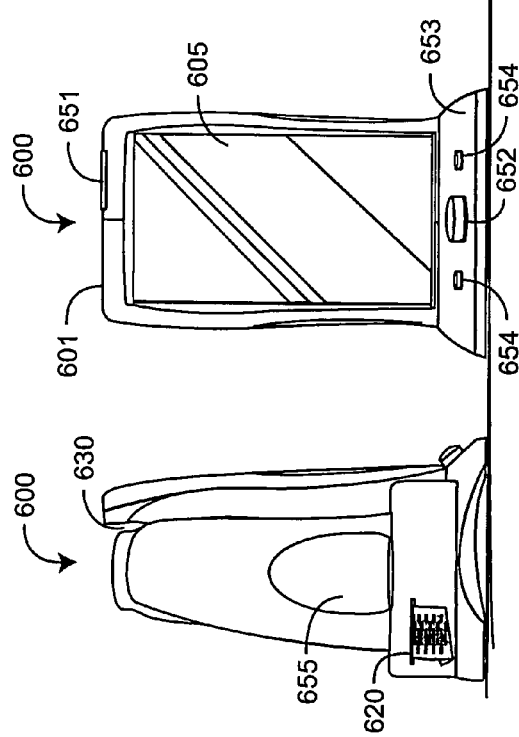

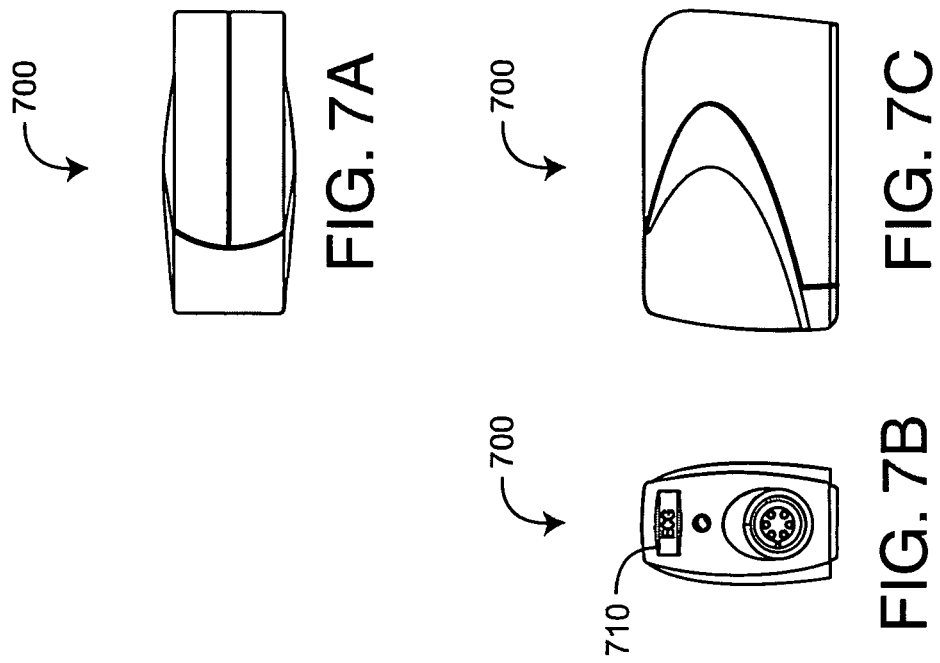

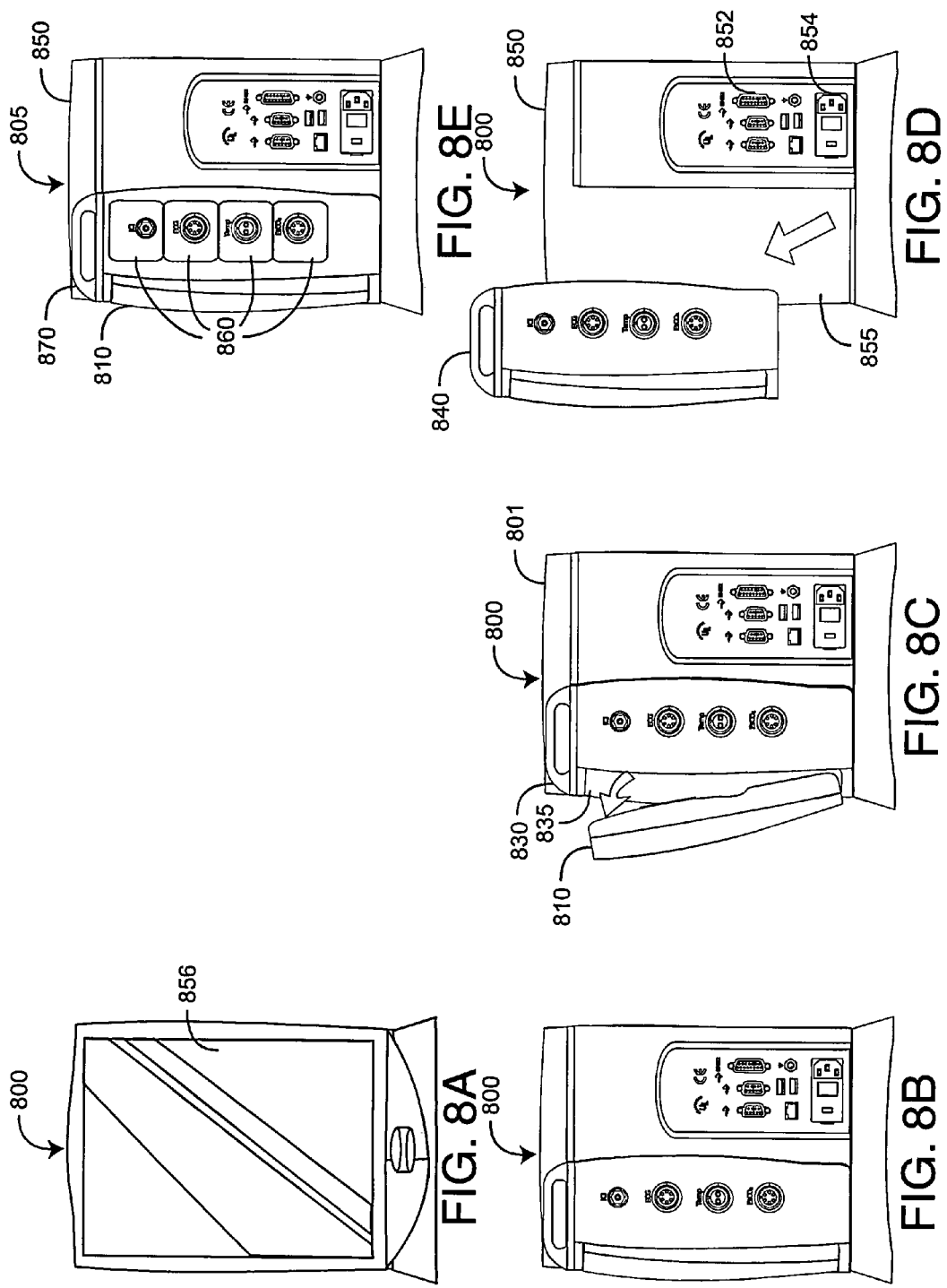

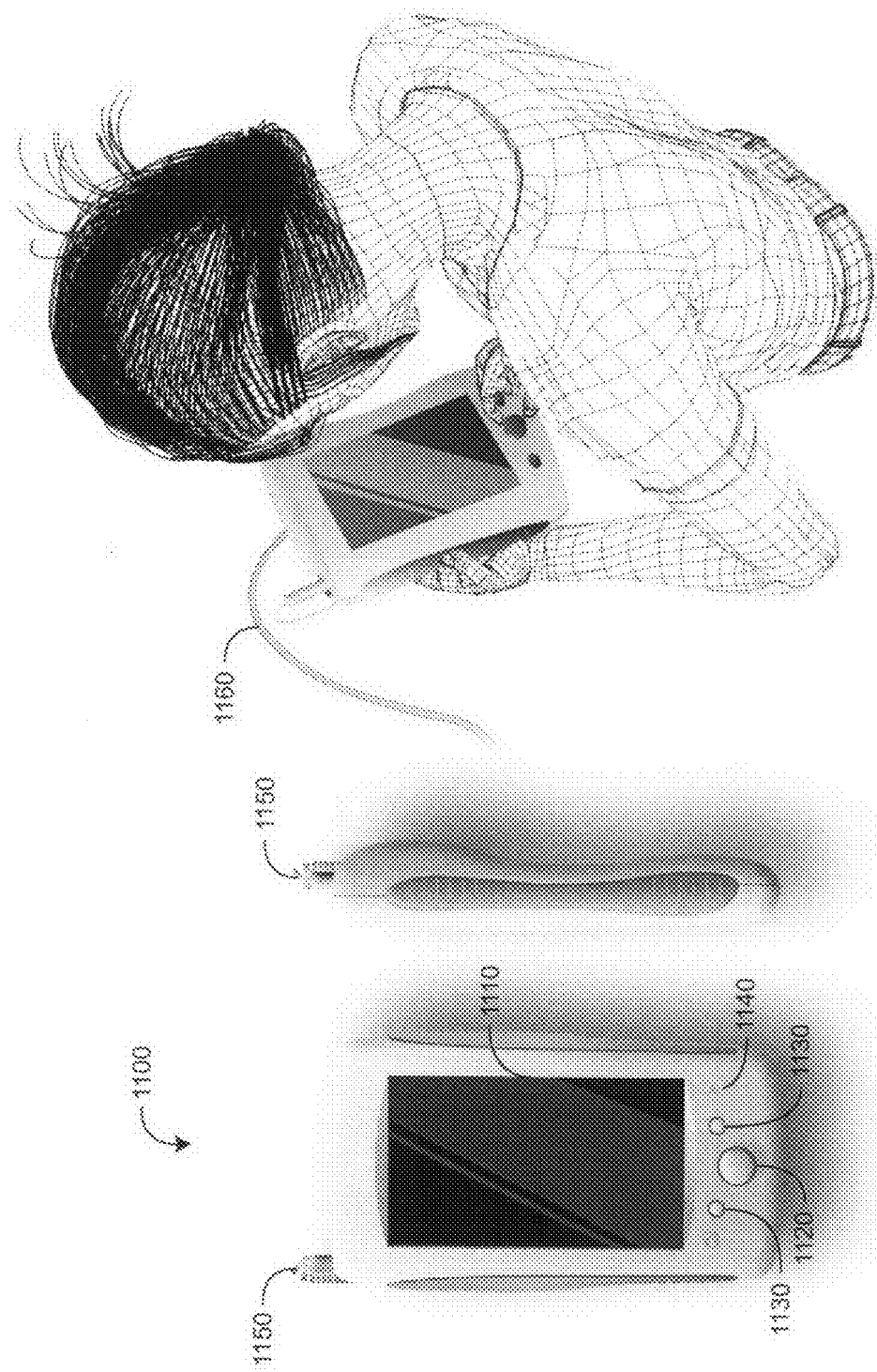

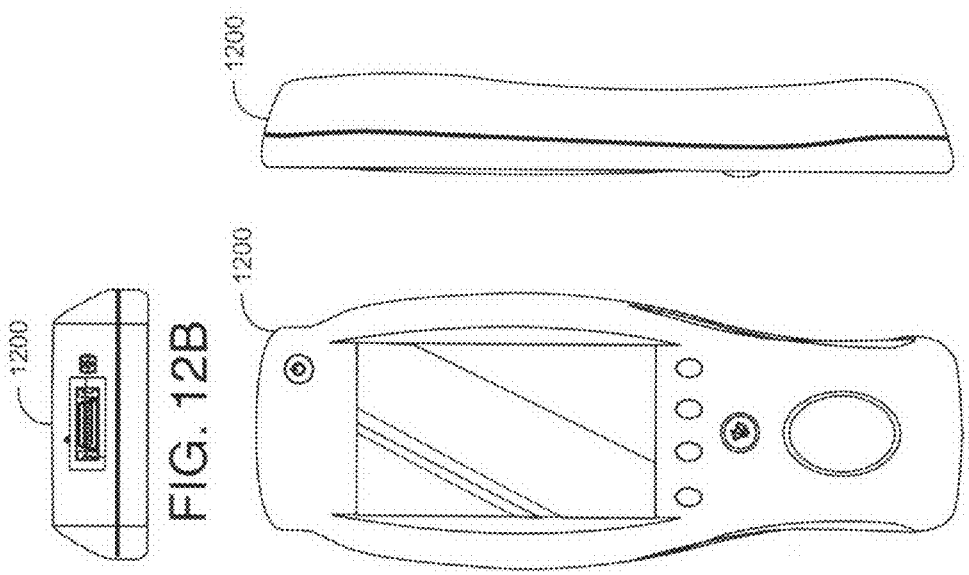
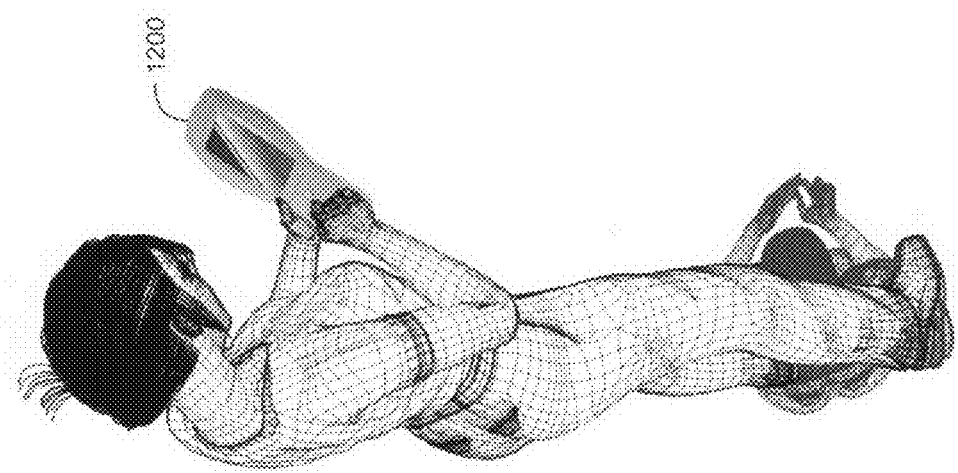

MODULAR PATIENT MONITOR

CROSS-REFERENCE TO RELATED APPLICATIONS

This application relates to and claims the benefit of prior U.S. Provisional Application No. 60/846,471, filed Sep. 22, 2006, entitled Modular Patient Monitor, incorporated by reference herein.

BACKGROUND OF THE INVENTION

Pulse oximetry is a widely accepted continuous and non-invasive method of measuring the level of arterial oxygen saturation in blood. A typical pulse oximetry system has a sensor, a patient monitor and a patient cable. The sensor is placed on a patient fleshy tissue site, usually on the fingertip for adults and the hand or foot for neonates and connected to the patient monitor via the patient cable. The sensor provides a sensor signal detected from the patient tissue site to the patient monitor. The patient monitor displays the calculated data as a percentage value for arterial oxygen saturation ($SpO_2$), as a pulse rate (PR) and as a pulse waveform (plethysmograph or "pleth").

SUMMARY OF THE INVENTION

A modular patient monitor provides a multipurpose, scalable solution for various patient monitoring applications. In an embodiment, a modular patient monitor utilizes multiple wavelength optical sensor and acoustic sensor technologies to provide blood constituent monitoring and acoustic respiration monitoring (ARM) at its core, including pulse oximetry parameters and additional blood parameter measurements such as carboxyhemoglobin (HbCO) and methemoglobin (HbMet). Pulse oximetry monitors and sensors are described in U.S. Pat. No. 5,782,757 entitled Low Noise Optical Probes and U.S. Pat. No. 5,632,272 entitled Signal Processing Apparatus, both incorporated by reference herein. Advanced blood parameter monitors and sensors providing blood parameter measurements in addition to pulse oximetry are described in U.S. patent application Ser. No. 11/367,013, filed Mar. 1, 2006 entitled Multiple Wavelength Sensor Emitters and U.S. patent application Ser. No. 11/367,014, filed Mar. 1, 2006 entitled Non-Invasive Multi-Parameter Monitor, both incorporated by reference herein. Acoustic respiration sensors and monitors are described in U.S. Pat. No. 6,661,161 entitled Piezoelectric Biological Sound Monitor with Printed Circuit Board and U.S. patent application Ser. No. 11/547,570 filed Oct. 6, 2006 entitled Non-Invasive Monitoring of Respiration Rate, Heart Rate and Apnea, both incorporated by reference herein.

Expansion modules provide blood pressure BP, blood glucose, ECG, $CO_2$, depth of sedation and cerebral oximetry to name a few. The modular patient monitor is advantageously scalable in features and cost from a base unit to a high-end unit with the ability to measure multiple parameters from a variety of sensors. In an embodiment, the modular patient monitor incorporates advanced communication features that allow interfacing with other patient monitors and medical devices.

The modular patient monitor is adapted for use in hospital, sub-acute and general floor standalone, multi-parameter measurement applications by physicians, respiratory therapists, registered nurses and other trained clinical caregivers. It can be used in the hospital to interface with central monitoring and remote alarm systems. It also can be used to obtain routine vital signs and advanced diagnostic clinical information and as an in-house transport system with flexibility and portability for patient ambulation. Further uses for the modular patient monitor are clinical research and other data collection.

BRIEF DESCRIPTION OF THE DRAWINGS

FIGS. 1A-E are top, side, front, right and back views of a modular patient monitor;

FIGS. 6A-E are top, side, front, right and back views of another modular patient monitor embodiment having alternative cartridge embodiments;

FIGS. 7A-C are top, front and side views of an alternative cartridge embodiment;

FIGS. 8A-E are a front and various back views of yet another modular patient monitor embodiment having a shuttle, including a display and control; a docked shuttle; a docked shuttle with an undocked handheld; an undocked shuttle; and a shuttle having a handheld;

FIGS. 11A-C are illustrations of a tablet-configured handheld monitor;

FIGS. 12A-D are front perspective, top, front and side views of an alternative handheld embodiment;

DETAILED DESCRIPTION OF THE PREFERRED EMBODIMENTS

Figure 2A:
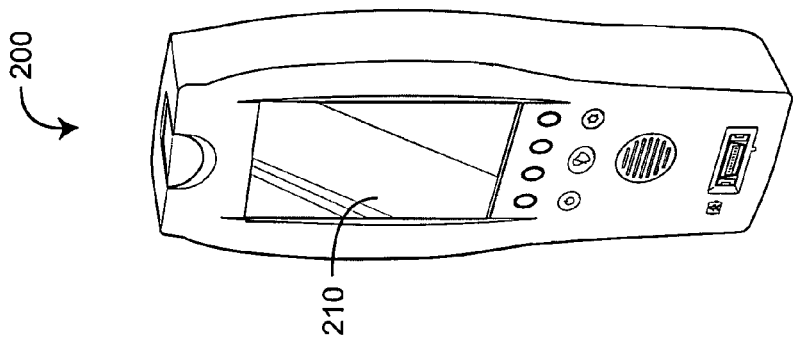
FIGS. 2A-B are front and perspective views of a handheld monitor.

FIGS. 1A-E illustrate a modular patient monitor embodiment 100 having a two-piece modular configuration, a handheld 200 unit and a configurable docking station 101. The handheld 200 docks into a handheld port 110 of the docking station 101, providing the modular patient monitor 100 with two-in-one functionality. In particular, the handheld 200 provides a specific set of clinically relevant parameters. The docking station 101 supports various parameters that are configured to specific hospital environments and/or patient populations including general floor, OR, ICU, ER, NICU, to name a few. Further, the docking station 101 has module ports 120 that accept plug-in expansion modules 500 for additional parameters and technologies. The handheld 200 docked into the docking station 101 allows access to all available parameters providing maximum connectivity, functionality and a larger color display 300. The modular patient monitor 100 provides standalone multi-parameter applications, and the handheld 200 is detachable to provide portability for patient ambulation and in-house transport.

As shown in FIGS. 1A-E, the docking station 101 has a dashboard 130, with a trim knob 140 and buttons 150 so as to support system navigation and data entry. The trim knob 140 is a primary means for system navigation and data entry with an option of a keyboard and mouse as a secondary means.

The docking station 101 also has a power supply module 160 and connectivity ports 170. The handheld 200 mechanically attaches to and electrically connects to the docking station 101 when docked, such that the two devices function as one unit and both the handheld display 210 and the docking station display 300 provide user information. In an embodiment, the handheld 200 docks on a docking station side such that the handheld display 200 is visible from that side of the docking station 101 (FIG. 1D). In addition, the docking station 101 has one or more module slots 120 that accommodate external modules 400, as described with respect to FIGS. 4A-C, below.

Also shown in FIGS. 1A-E, controls of the docking station 101 take precedence over those of the handheld 200 when docked. However, the handheld buttons 220 also work for back up purposes. In an embodiment, buttons 150, 220 on the docking station dashboard 130 and on the handheld 200 provide for alarm suspend/silence and mode/enter. The trim knob 140 is the primary method to toggle thru screen menus on the dashboard 130. The procedure includes next, up, down or across page navigation, parameter selection and entry, data entry, alarm limit selection and selection of probe-off detection sensitivity. As a secondary control method, the modular patient monitor 100 has a port for an external keyboard for patient context entry and to navigate the menu. In an embodiment, the docking station 150 has a touch screen. In an embodiment, the modular patient monitor 100 has a bar code scanner module adapted to automatically enter patient context data.

The modular patient monitor 100 includes an integral handle for ease of carrying and dead space for storage for items such as sensors, reusable cables, ICI cable and cuff, $EtCO_2$ hardware and tubing, temperature disposables, acoustic respiratory sensors, power cords and other accessories such as ECG leads, BP cuffs, temperature probes and respiration tapes to name a few. The monitor 100 can operate on AC power or battery power. The modular patient monitor 100 stands upright on a flat surface and allows for flexible mounting such as to an anesthesia machine, bedside table and computer on wheels.

Figure 2B:
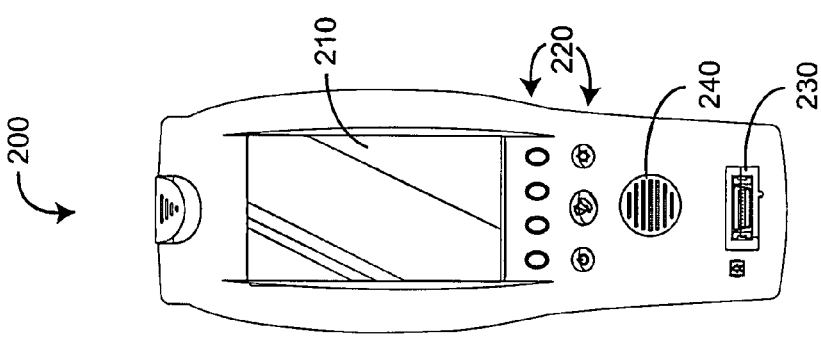

FIGS. 2A-B illustrate a handheld monitor 200, which provides pulse oximetry parameters including oxygen saturation ($SpO_2$), pulse rate (PR), perfusion index (PI), signal quality (SiQ) and a pulse waveform (pleth), among others. In an embodiment, the handheld 200 also provides measurements of other blood constituent parameters that can be derived from a multiple wavelength optical sensor, such as carboxyhemoglobin (HbCO) and methemoglobin (HbMet). The handheld 200 has a color display 210, user interface buttons 220, an optical sensor port 230 and speaker 240. The handheld 200 also has external I/O such as a bar code reader and bedside printer connectivity. The handheld 200 also has a flexible architecture, power and memory headroom to display additional parameters, such as $Sp_vO_2$, blood glucose, lactate to name a few, derived from other noninvasive sensors such as acoustic, fetal oximetry, blood pressure and ECG sensors to name a few. In an embodiment, the handheld unit 200 has an active matrix (TFT) color display 210, an optional wireless module, an optional interactive touch-screen with on-screen keyboard and a high quality audio system. In another embodiment, the handheld 200 is a Radical or Radical-7™ available from Masimo Corporation, Irvine Calif., which provides Masimo SET® and Masimo Rainbow™ parameters. A color LCD screen handheld user interface is described in U.S. Provisional Patent Application No. 60/846,472 titled Patient Monitor User Interface, filed Sep. 22, 2006 and U.S. Pat. No. _____ titled Patient Monitor User Interface, filed Sep. 24, 2007, both applications incorporated by reference herein.

Figure 3:
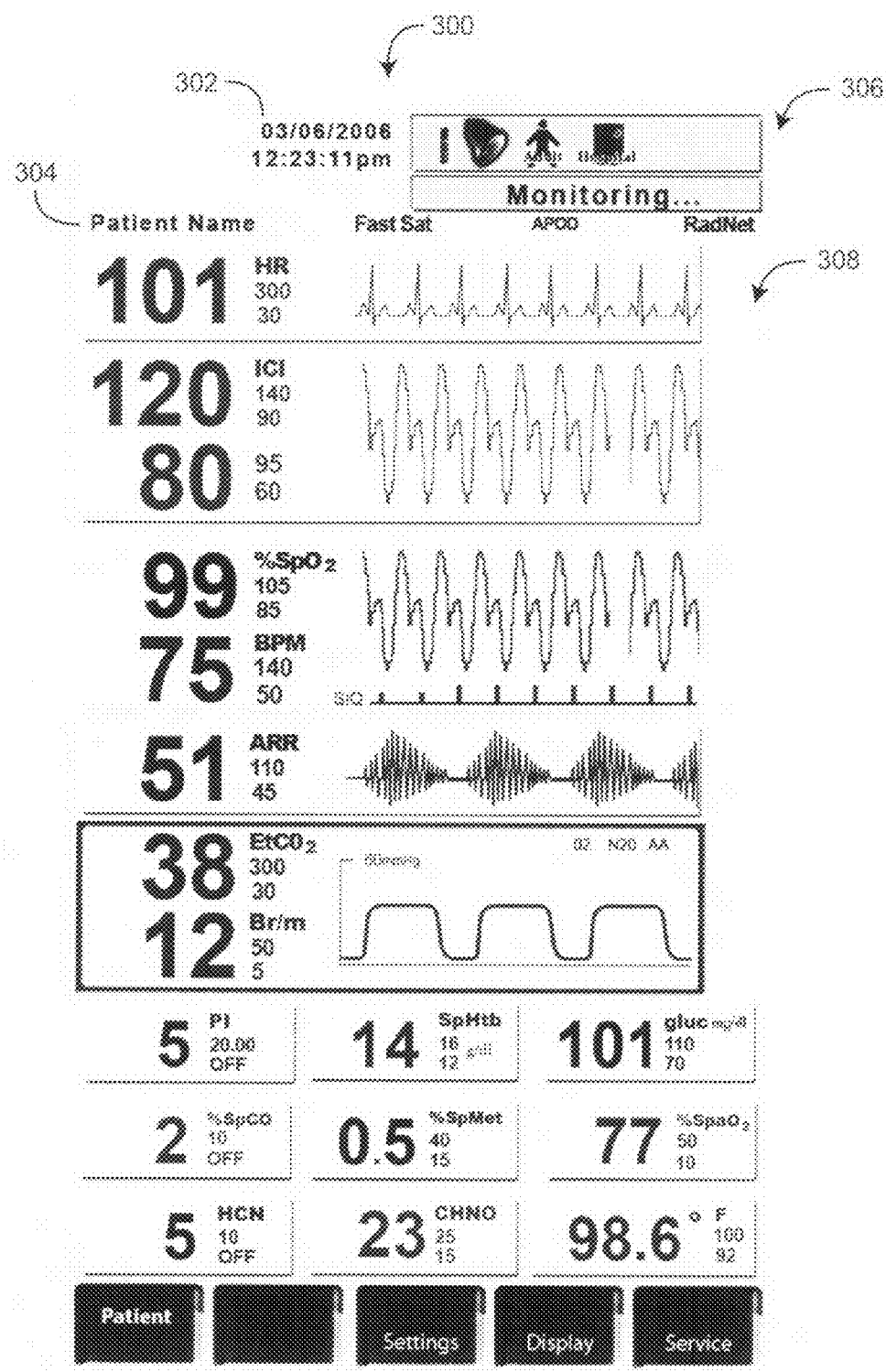
FIG. 3 is a docking station multiple parameter display.

FIG. 3 illustrates a modular patient monitor color display 300. The modular patient monitor display 300 auto-scales its presentation of parameter information based upon the parameters that are active. Fewer parameters result in the display 300 of larger digits and more waveform cycles. In an embodiment, the display 300 has a main menu screen showing date and time 302, patient data 304, battery life and alarm indicators 306 and all enabled parameters 308. Date and time 302 can be enabled or disabled. The display 300 may also have dynamic bar graphs or indicators to show perfusion index and signal quality. Waveforms are displayed for $SpO_2$, NIBP (non-invasive blood pressure), $EtCO_2$ (end-tidal carbon dioxide) and ECG (electrocardiogram) if enabled. Trend waveforms are displayed for parameters that are less dynamic, such as HbCO and HbMet. Further, the display 300 has individual text displays for alarms, alarm suspend, sensor off or no sensor, battery condition, sensitivity, trauma mode, AC power, printer function, recording function, connectivity messages and menus to name a few. Pulse search is indicated by blinking dashes in the pulse and parameter displays. In an embodiment, the color display 300 is an 11.1" LCD with allowance for the use of a 10.4" LCD within the standard mechanical design for the 11.1" display. The docking station 101 also supports any external VGA display.

An exemplar color print illustration of the color display 300 is disclosed in U.S. Provisional Application No. 60/846,471 entitled Modular Patient Monitor, cited above. In particular, each of the displayed parameters are variously presented in one of a off-white to white shade, lime green to green shade, crimson to red shade, generally turquoise shade, generally chartreuse shade, yellow to gold shade, generally blue and generally purple shade, to name a few.

Figure 4:
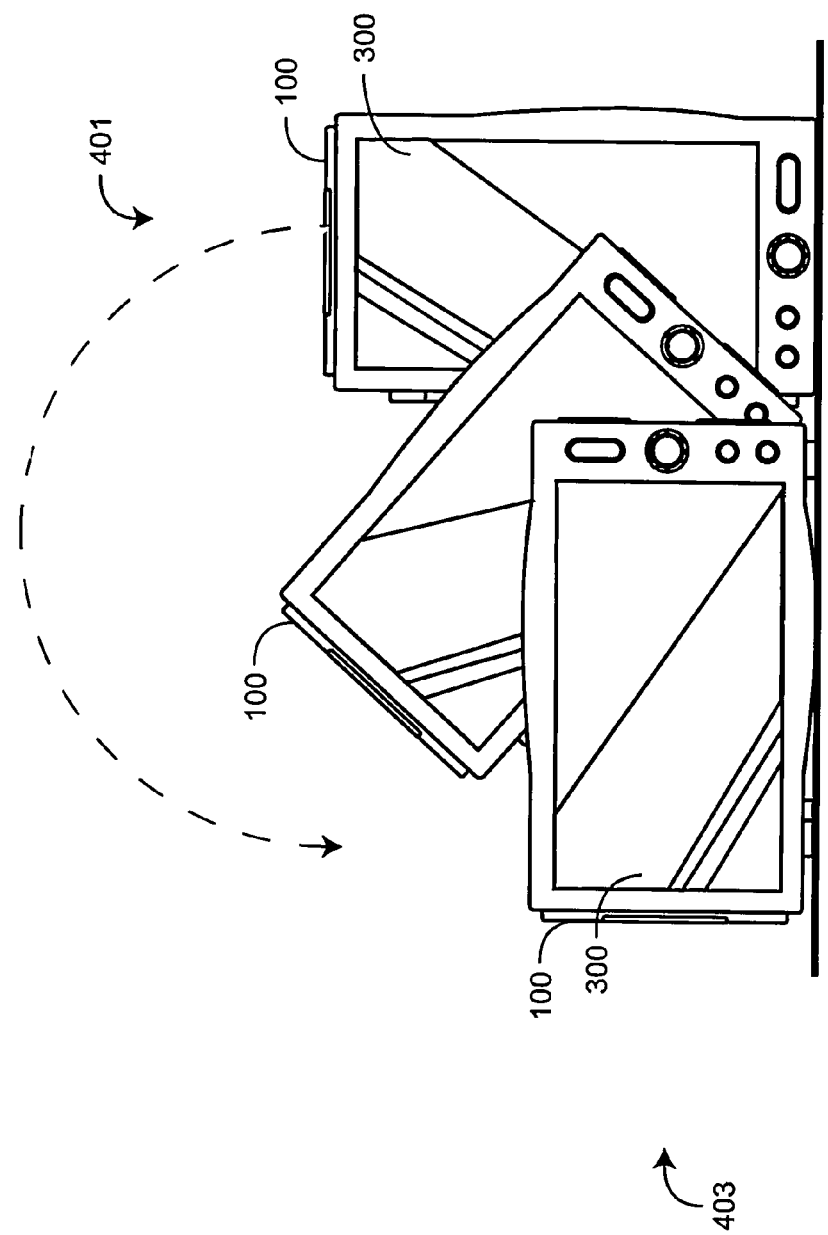
FIG. 4 is an illustration of a modular patient monitor having 90 degree rotation with corresponding display rotation.

FIG. 4 illustrates a modular patient monitor 100 having a vertical orientation 401 and a horizontal orientation 403. In the vertical orientation 401, the display 300 presents data in a vertical format, such as shown in FIG. 3, above. In the horizontal orientation 403, the display 300 presents data in a horizontal format, so that the data appears upright with respect to the viewer. That is, the display 300 automatically switches format according to the patient monitor 100 orientation. A patient monitor having a rotatable display format is described in U.S. Pat. No. 6,770,028 entitled Dual Mode Pulse Oximeter and incorporated by reference herein.

Figure 5A:
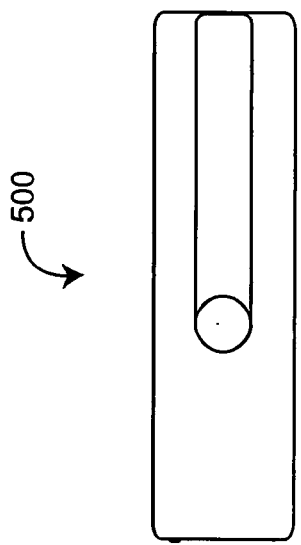
FIGS. 5A-C are top, front and side views of a monitor cartridge.
Figure 5C:
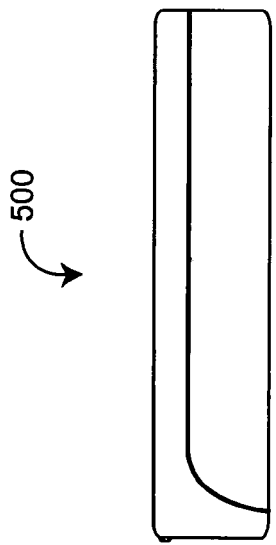
Figure 5B:
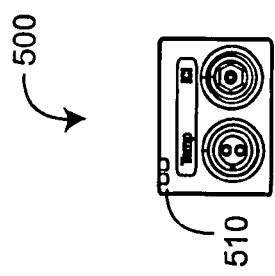

FIGS. 5A-C illustrate an expansion module 500, which the docking station 101 (FIGS. 1A-E) accepts for additional parameters and technologies, such as ICI-NIBP, glucose monitoring, ECG, $EtCO_2$, conscious sedation monitoring, cerebral oximetry, anesthetic agent monitoring, lactate, patient body temperature and assay cartridges, to name a few. The expansion module 500 has an indicator 510 indicating parameters to be provided. In one embodiment, the expansion module 500 provides two parameters to the docking station, which is adapted to accept two modules 500 for four additional parameters. In an embodiment, an ECG module is used to provide an R-wave trigger for ICI-NIBP.

As shown in FIGS. 1A-E, the modular patient monitor 100 includes various connectivity ports 170 such as Ethernet, USB, RS-232, RS-423, nurse call, external VGA and I/O ports for a keyboard and a bar code reader to name a few. As an option, the modular patient monitor 100 has on-board and bedside recorder capability. The modular patient monitor 100 also supports multiple wireless and hardwired communication platforms, web server technology that allows remote viewing of data as well as limited bi-directional control of module functionality and an optional wireless connectivity standards base technology, such as IEEE 802.11x. The wireless option is provided in the handheld 200 and the docking station 101. A wireless module supports the downloading and temporary storage of upgrade software from a remote central server to a destination docking station or a specific module. In an embodiment, the modular patient monitor 100 supports patient context management, specifically the ability to upload or alternatively enter patient unique identification. The modular patient monitor 100 also connects both wired and wirelessly to other patient monitors.

The modular patient monitor 100 may be logged onto via the Internet so as to download raw waveforms and stored trending data for both customer service purposes and for data mining to enhance algorithms and so as to be uploaded with firmware updates. The modular patient monitor 100 may also incorporate removable storage media for the same purpose. In an embodiment, removable storage media functions as a black box, which is a diagnostic tool to retrieve device use information. In particular, the black box can record values displayed, raw waveforms including sounds, and buttons touched by the end user. A patient monitor with removable storage media is described in U.S. patent Ser. No. 10/983,048 entitled Pulse Oximetry Data Capture System filed Nov. 5, 2004 and incorporated by reference herein.

The modular patient monitor 100 may also have an audio module slot (not shown) accommodating an external audio system and wireless headphone module. In an embodiment, the docking station 101 audio system is configured to reproduce respiratory sounds from an ARR (acoustic respiratory rate) sensor.

In an embodiment, the modular patient monitor 100 has a redundant speaker system for alarms. The modular patient monitor 100 may also include alarms for all parameters and a parameter fusion alarm that involves analysis of multiple parameters in parallel. A user can select custom default alarm parameters for adult, pediatric and neonatal patients. A patient monitor having redundant alarm speakers is described in U.S. patent application Ser. No. 11/546,927 entitled Robust Alarm System, filed Oct. 12, 2006 and incorporated by reference herein.

An alarm condition exists for low battery, sensor-off patient, defective sensor, ambient light, parameter limit exceeded and defective speakers, as examples. Audible alarm volume is adjustable and when muted, a visual indicator is illuminated. In an embodiment, the volume is adjustable in at least of four discrete steps. The parameter display flashes to indicate which values are exceeding alarm limits, the parameter is enlarged automatically, and numerics are displayed in either RED or with a RED background. The audible alarm is silence-able with a default alarm silence period for up to two minutes. This delay can be user configurable. Separate from sleep mode, the audible alarms are permanently mutable via a password-protected sub-menu. The visual alarm indicator still flashes to indicate an alarm condition. A visual indicator on the dashboard indicates an alarm silence condition, such as blinking for temporary silence and solid for muted. An alarm speaker is mounted so as not to be susceptible to muffling from a bed surface, attached external monitor surface or other type of flat resting surface. Redundant and smart alarm annunciation is also provided.

The user accesses the setup menu via a front dashboard knob 140 and mode/enter button 150. TABLE 1 shows user settable parameters. The user can override default settings on a patient-by-patient basis via setup menus.

TABLE 1

PARAMETER SETTINGS

| |
| --- |
| $SpO_2$ high & low limit |
| Pulse Rate high & low limit |
| Pulse Tone volume |
| MetHb high and low limit |
| HbCO high & low limit |
| ICI high and low limit |
| tHb high and low limit |
| $EtCO_2$ high and low limit |
| ARR high and low limit |
| Temp high and low limit |
| Glucose high and low limit |
| Audible alarm volume |

Default settings are stored in non-volatile memory (NVM). There is a factory, hospital and user default setting which may be automatically based on patient recognition. The user can choose any of the three at any time. The user may over-write hospital and user default settings with their own preferences via a password protected "save as default" setup menu function. All parameters return to hospital default settings after a power cycle.

In one embodiment, the default settings are as shown in TABLE 2, stored in NVM. These settings are also over-written into NVM as a result of a factory reset or return to factory defaults function from within the setup menus.

TABLE 2

| PARAMETER | FACTORY DEFAULT |
| --- | --- |
| SpO2 high limit | Off |
| SpO2 low limit | 90 |
| Pulse Rate high limit | 140 |
| Pulse Rate low limit | 40 |
| Alarm Volume | 2 (of 4) |
| Pulse tone volume | 2 (of 4) |
| MetHb high limit | 5% |
| MetHb low limit | Off |
| HbCO high limit | 10% |
| HbCO low limit | Off |
| LCD brightness | 3 (of 5) |

FIGS. 6A-E illustrate another modular patient monitor 600 embodiment having a docking station 601, a handheld monitor 602 and parameter cartridges 700. Each cartridge 700 provides one parameter to the docking station 601, which accepts four cartridges 700 for a total of four additional parameters. Further, the patient monitor 600 also has a cord management channel 630, an oral temperature probe 660 and probe covers 670 located on the docking station 601. The docking station 601 has a trim knob 652 and control buttons 654 on a front stand 653 so as to support system navigation and data entry. The docking station 601 also has a color display 605, a thermal printer 620, an alarm indicator light bar 651, a thermal printer paper door 657 and a handle 659, a sensor holder 655, connectivity ports 680 and a power supply module 690. FIGS. 7A-C illustrate a parameter cartridge 700 having an indicator 710 indicating the parameter or technology provided.

FIGS. 8A-D illustrate a three-piece modular patient monitor 800 including a handheld monitor 810, a shuttle station 830 and a docking station 850. The docking station 850 has a shuttle port 855 that allows the shuttle station 830 to dock. The shuttle station 830 has a handheld port 835 that allows the handheld monitor 810 to dock. Accordingly, the modular patient monitor 800 has three-in-one functionality including a handheld 810, a handheld 810 docked into a shuttle station 830 as a handheld/shuttle 840 and a handheld/shuttle 840 docked into a docking station 850. When docked, the three modules of handheld 810, shuttle 830 and docking station 850 function as one unit.

As shown in FIGS. 8A-D, the handheld module 810 functions independently from the shuttle 830 and docking station 850 and is used as an ultra-light weight transport device with its own battery power. The handheld 810 docked into the shuttle module 830 functions independently of the docking station 850 and expands the handheld parameter capability to the ability to measure all parameters available. The docking station 850, in turn, provides the shuttle 830 or handheld/shuttle 840 with connectivity ports 852, a power supply module 854, a large color display 856, wireless and hardwired communications platforms, a web server and an optional printer. As such, the docking station 850 charges the handheld 810 and shuttle 830, provides a larger screen and controls, such as a trim knob, allows wireless, hardwired and Internet communications and provides connectivity to various external devices. FIG. 8E illustrates another modular patient monitor embodiment 805 having a shuttle 870 with plug-in modules 860 for expanded parameter functionality.

In an embodiment, the handheld monitor 810 incorporates blood parameter measurement technologies including HbCO, HbMet, $SpO_2$ and Hbt, and the shuttle station 830 incorporates non-blood parameters, such as intelligent cuff inflation (ICI), end-tidal $CO_2$ ($EtCO_2$), acoustic respiration rate (ARR), patient body temperature (Temp) and ECG, to name a few. In an alternative embodiment, parameters such as $SpO_2$, ARR and ECG that clinicians need during in-house transports or patient ambulation are loaded into the handheld 810.

Figure 9:
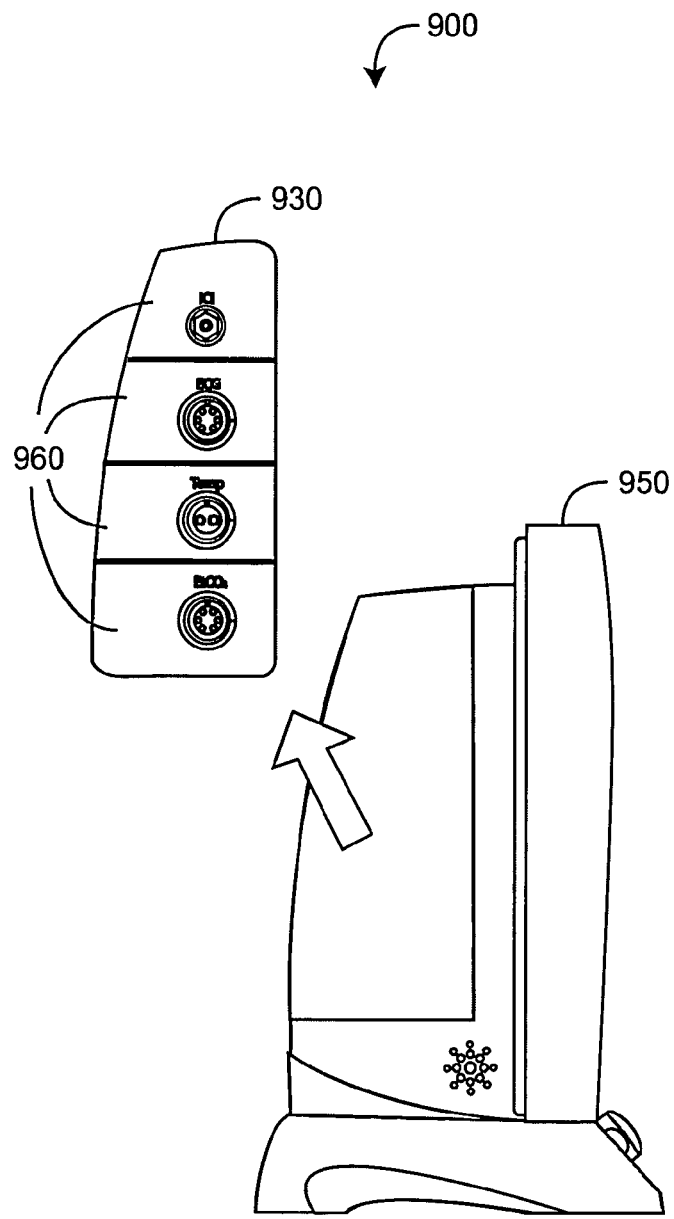
FIG. 9 is a modular patient monitor side view of a further modular patient monitor embodiment having a shuttle without a docking handheld.

FIG. 9 illustrates a two-piece modular patient monitor 900 having a shuttle 930 and a docking station 950 without a corresponding handheld. In an embodiment, the shuttle 930 has plug-in modules 960 for added parameter functions.

Figures 10A, 10B, 10C:
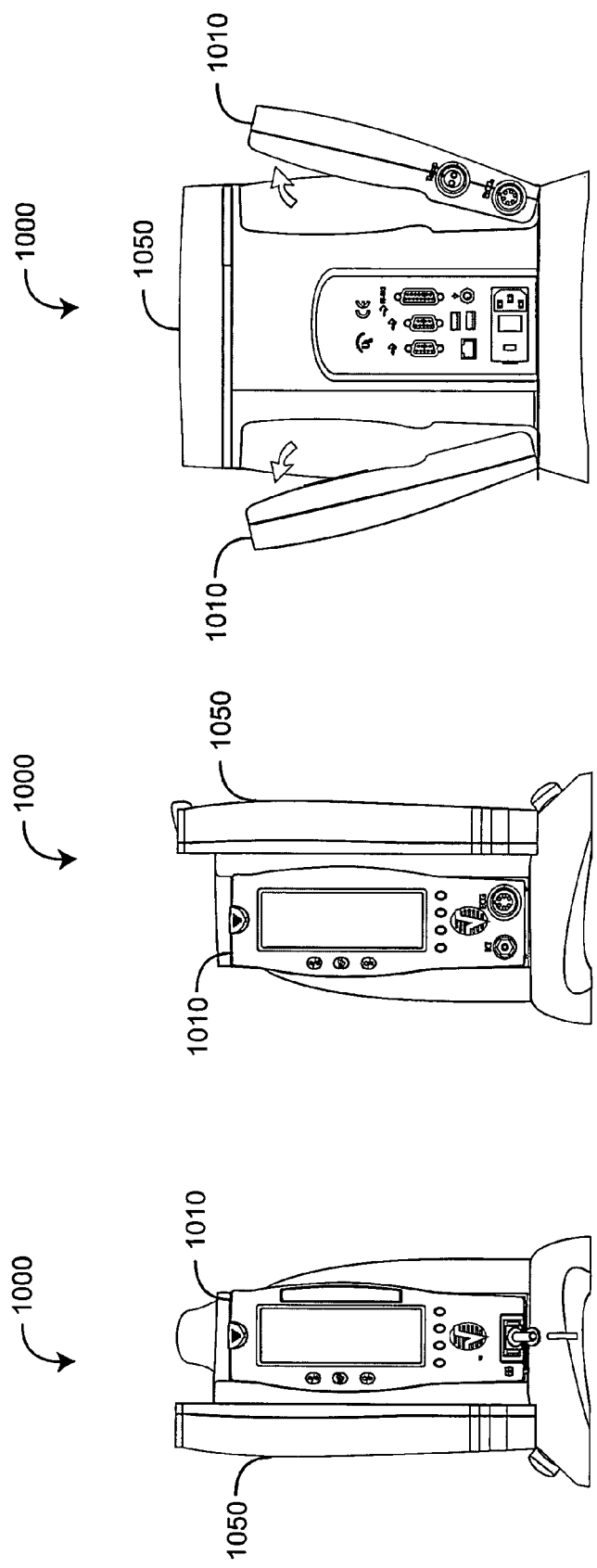
FIGS. 10A-C are side views and a back view, respectively, of an additional modular patient monitor embodiment having dual dockable handhelds.

FIGS. 10A-C illustrate yet another modular patient monitor 1000 embodiment having dual removable handhelds 1010 and a docking station 1050 without a corresponding shuttle. For example, the handhelds 1010 may include one blood parameter monitor and one non-blood parameter monitor.

Figure 13A:
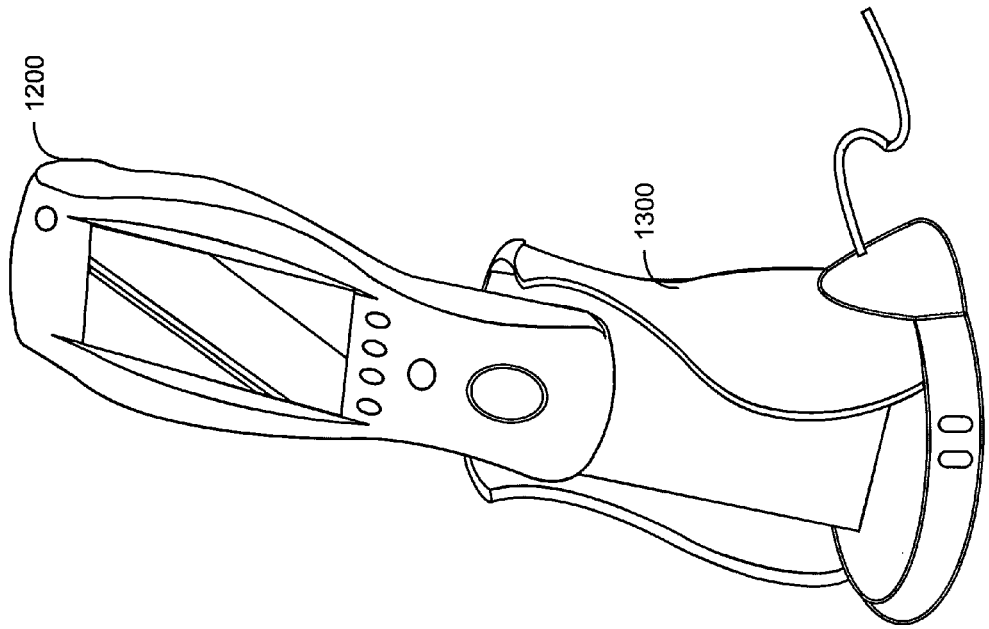
FIGS. 13A-B are front perspective views of an alternative handheld embodiment plugged into, and removed from, a charger.
Figure 13B:
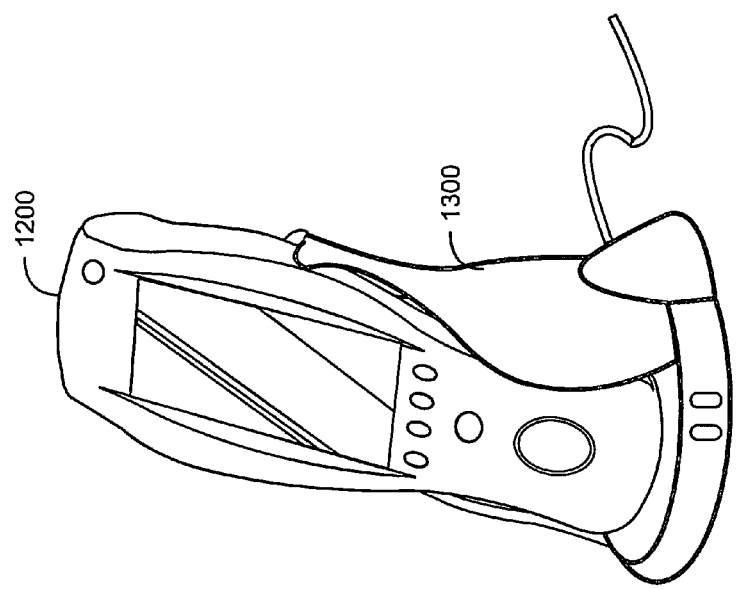

FIGS. 11A-C illustrate a handheld tablet monitor 1100 having a display 1110, a trim knob 1120 and control buttons 1130. An electroluminescent lamp 1140 on the front panel provides a thin uniform lighting with low power consumption. A temperature probe 1150 is attached to the monitor 1100. The tablet monitor 1100 connects to a multiple parameter sensor through a patient cable 1160. FIGS. 12-13 illustrate a handheld monitor 1200 configured to plug into a compact holder/battery charger 1300. The handheld monitor 1200 is adapted to plug into the compact charger 1300.

Figure 14:
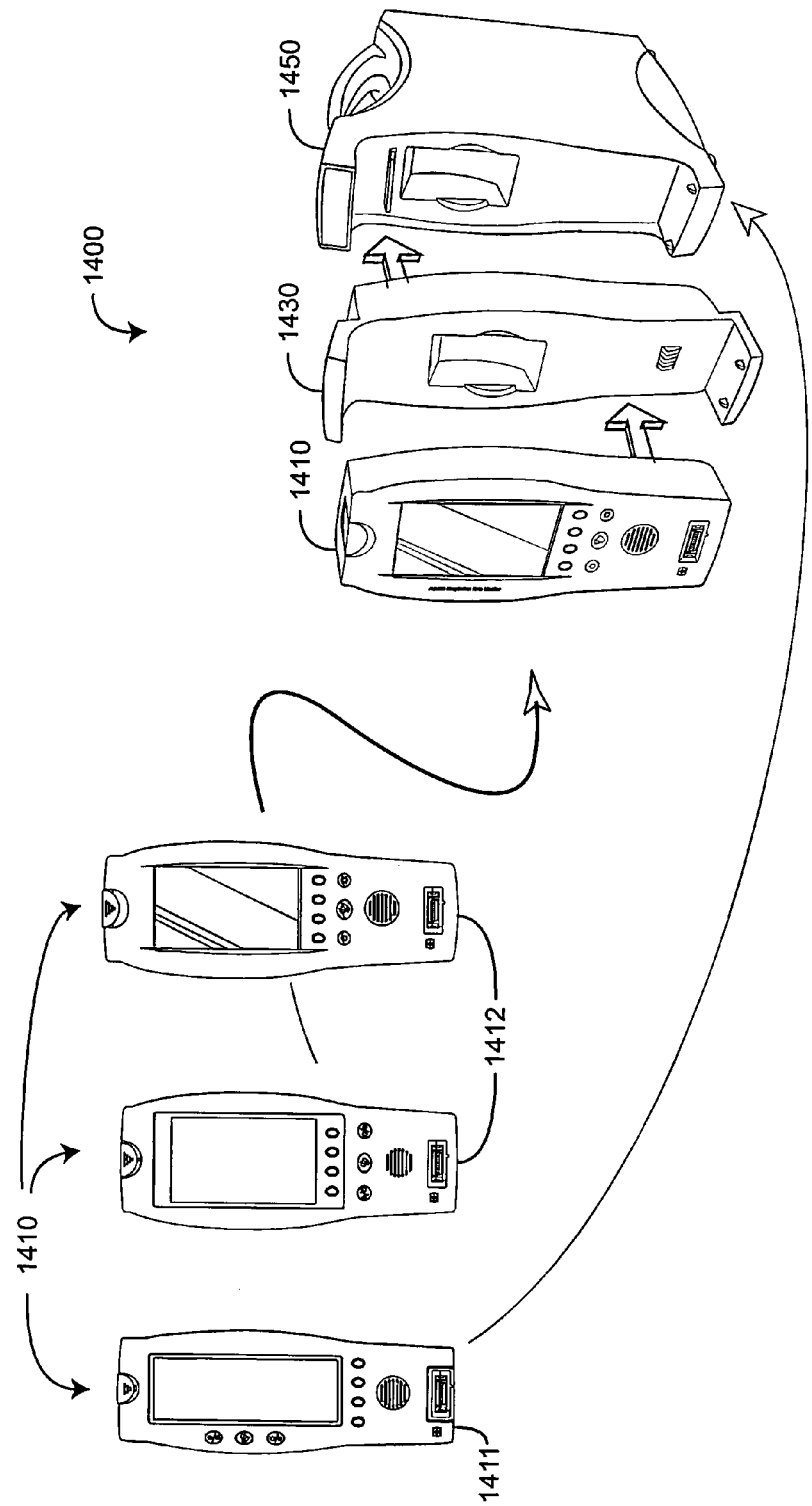
FIG. 14 is a perspective view of upgrade and legacy handhelds installable into a legacy docking station directly or via a docking station adapter.

FIG. 14 illustrates a modular patient monitor 1400 embodiment having various handheld monitors 1410, a docking station adapter 1430 and a legacy docking station 1450. The handheld monitors 1410 can include legacy handhelds 1411 and upgrade handhelds 1412. The docking station adapter 1430 is configured for the legacy docking station 1450 so that both legacy handhelds 1411 and upgrade handhelds 1412 can dock into the legacy docking station 1450 directly or via the docking station adapter 1430.

Figure 15A:
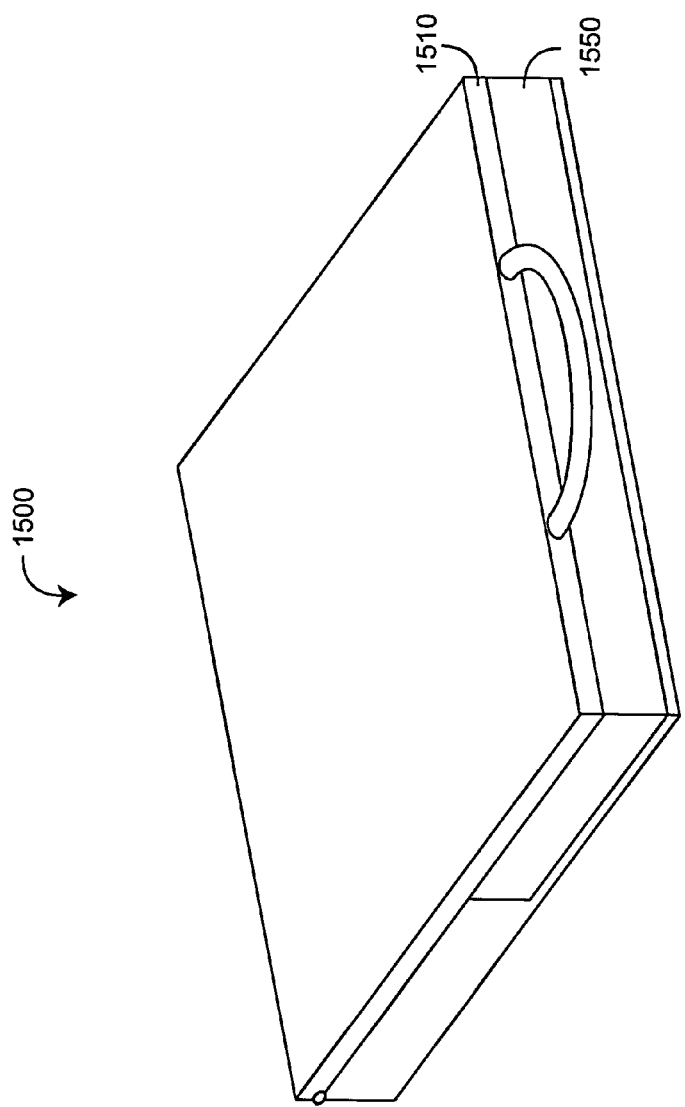
FIGS. 15A-B are closed and opened views, respectively, of a notebook-style modular patient monitor embodiment having a foldable display.
Figure 15B:
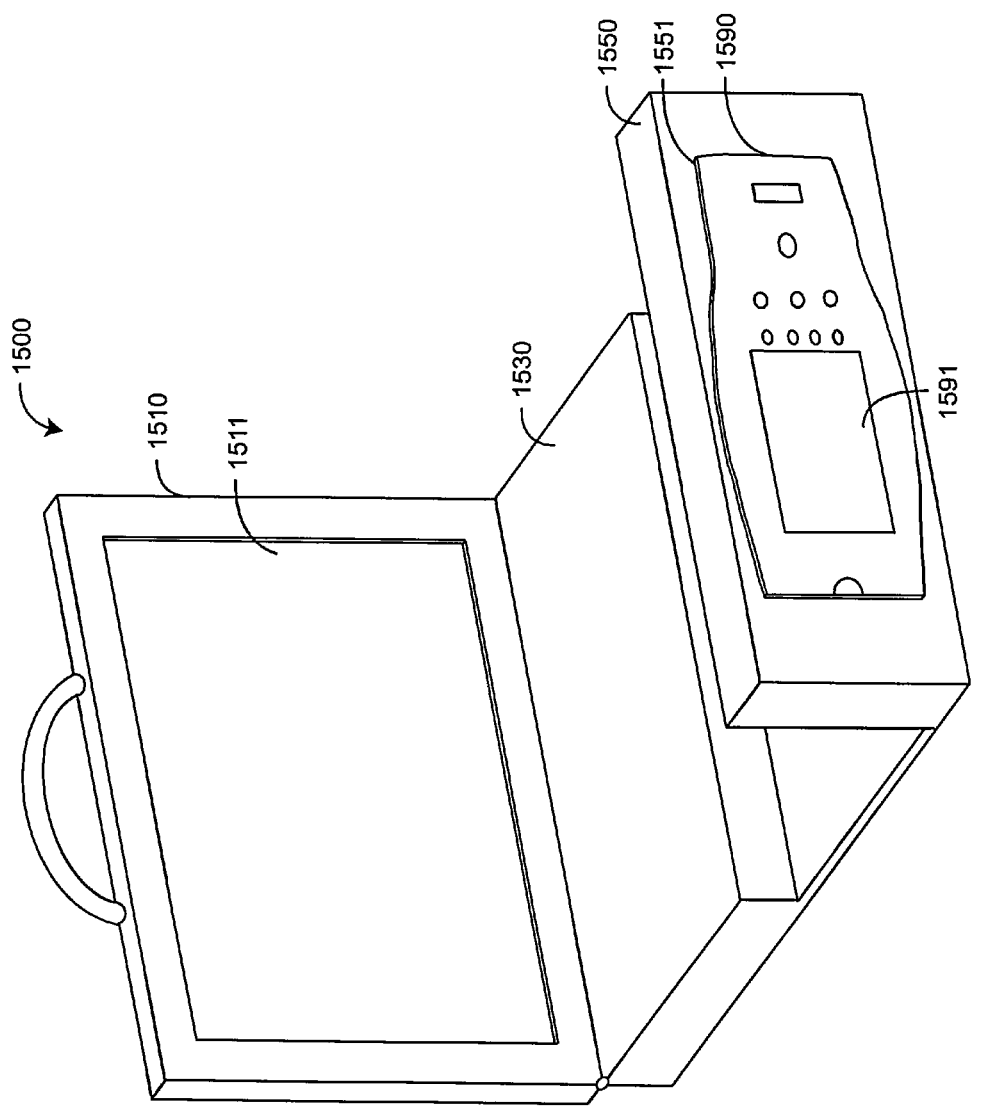

FIGS. 15A-B illustrate a "notebook" modular patient monitor 1500 embodiment having a foldable lid 1510, a fixed body 1530 and a foldable docking station 1550. The fixed body 1530 houses patient monitor electronics and provides external device connectivity at a back end (not visible). The lid 1510 has a notebook display 1551, such as a color LCD. The docking station 1550 has a port 1551 that removably connects, both mechanically and electrically, a corresponding handheld monitor 1590, such as the handheld embodiments described above. In a closed position (FIG. 15A), the notebook monitor 1500 can be carried via an optional handle or simply in hand or under an arm. In an open position (FIG. 15B), the notebook monitor is operational, connecting to patient sensors via the handheld 1590 or a sensor connector (not shown) on the back end of the notebook. In the open position, the docking station 1550 can stay in a stowed or folded position (not shown) so that the handheld screen 1591 faces upward. Alternatively, in the open position, the docking station 1550 is unfolded as shown (FIG. 15B) so that the handheld display 1591 can be easily viewed from the front of the notebook in conjunction with the notebook display 1511 in the lid 1510. In an embodiment, the notebook 1500 can have a conventional keyboard and touch pad, have conventional monitor controls, incorporate a conventional computer and peripherals or a combination of the above. As shown, the notebook display 1511 faces inward, so that the display 1511 is protected in the folded position. In another embodiment, the display 1511 faces outward (not shown).

Figure 16:
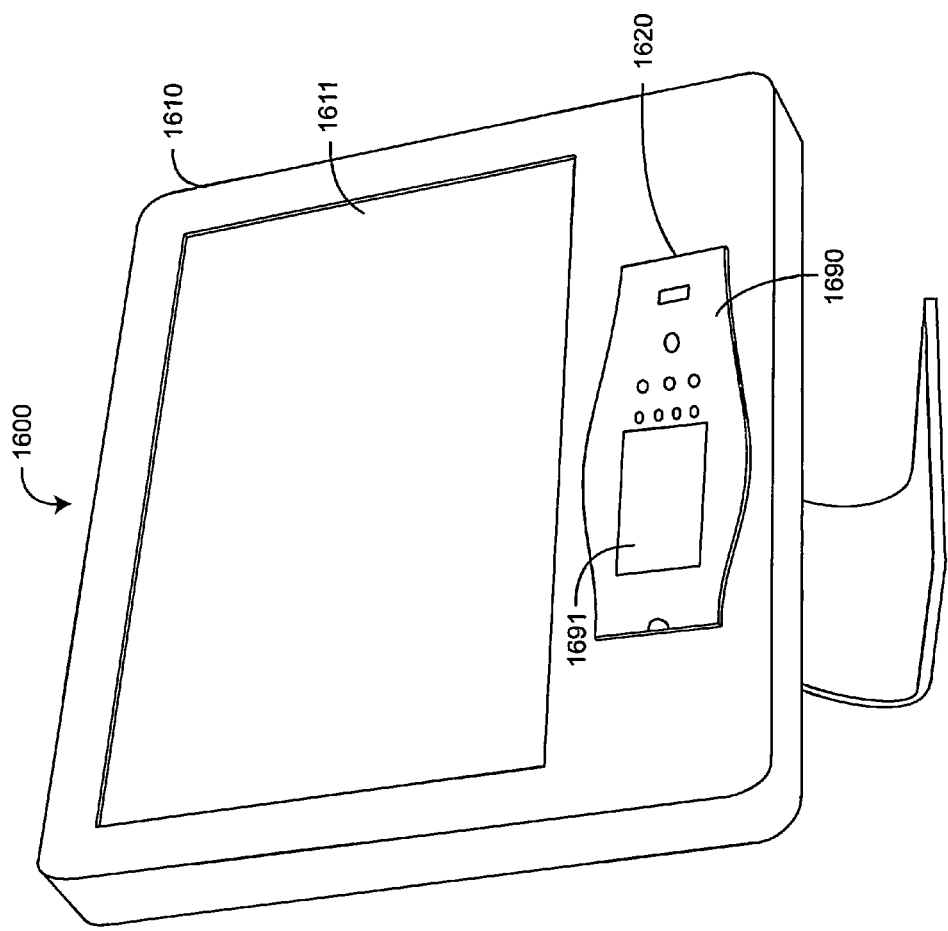
FIG. 16 is a perspective view of a flat panel display docking station.

FIG. 16 illustrates a flat panel modular patient monitor embodiment 1600 having a flat panel body 1610 housing a flat panel display 1611 and a handheld port 1620. The handheld port 1620 removably accepts a handheld monitor 1690 having a handheld display 1691, such as the handheld monitors described above. The flat panel monitor 1600 can be freestanding on a table top, wall-mounted or mounted on or integrated within a patient bed, as a few examples. The flat panel monitor 1600 can be simply a docking and display device or can provide built-in patient monitoring functions and parameters not available to the handheld 1690.

A modular patient monitor has been disclosed in detail in connection with various embodiments. These embodiments are disclosed by way of examples only and are not to limit the scope of the claims that follow. One of ordinary skill in art will appreciate many variations and modifications.

What is claimed is:

1. A modular patient monitor comprising:
a docking station including a first display integrated with said docking station, a docking port and a housing, said first display occupying substantially all of a display side of said housing, said docking station receives patient data, determines measurements for a first set of physiological parameters by processing said patient data, and displays at least some of said measurements on said first display; and
a handheld monitor including a second display integrated with said handheld monitor, said monitor receives patient data, determines measurements for a second set of physiological parameters by processing said patient data, and displays at least some of said measurements on said second display, at least some of the second set of parameters are the same as at least some of the first set of parameters, wherein said docking accepts the handheld monitor, the docking station functionally combining the first set of parameters and the second set of parameters whenever the handheld monitor is docked in the docking port, and at least a portion of the combined first and second sets of parameters are displayed on the first display integrated with the docking station including at least some of said same parameters from said first and second set of parameters.

2. The modular patient monitor according to claim 1 comprising
an expansion module having computational functionality for at least one physiological parameter, wherein said docking station further comprises
a module port, wherein when said expansion module is docked in said module port, the docking station adds the computational functionality for the at least one physiological parameter to the first set of parameters.

3. The modular patient monitor according to claim 2 wherein:
the second set of parameters are blood constituent related; and
the expansion module at least one physiological parameter is non-blood related.

4. The modular patient monitor according to claim 3 wherein the second display integrated with the handheld monitor is viewable simultaneously with the first display integrated with the docking station when the handheld monitor is docked in the docking station port.

5. The modular patient monitor according to claim 4 further comprising:
a second handheld monitor including a third display integrated with said second handheld monitor, said monitor receives patient data, determines measurements for a third set of parameters by processing said patient data, and displays at least some of the measurements on said third display, wherein at least some of the third set of parameters are the same as at least some of the first and second sets of parameters; and
a second docking station port on the docking station configured to accept the second handheld monitor.

6. A modular patient monitor comprising:
a docking station having a first display integrated with said docking station and a docking station port, the docking station providing patient monitoring functionality with respect to a first set of physiological parameters including an indication of blood oxygen saturation of a patient being monitored; and a handheld monitor removably attachable mechanically and electrically to the docking station via the docking station port, the handheld having a second display, the handheld monitor providing patient monitoring functionality with respect to a second set of parameters including one or more of blood pressure, other blood parameters, ECG, and respiration, wherein the patient monitoring functionality of the docking station includes the first and second set of parameters when the handheld monitor is docked in the docking station port.

7. The modular patient monitor according to claim 6 wherein the first display and the docking station together comprise a flat panel display incorporating the docking station port.

8. The modular patient monitor according to claim 6 wherein a notebook device is said docking station, wherein said notebook device comprises a foldable display and a foldable docking portion.

9. The modular patient monitor according to claim 7 wherein first display and second display are visible simultaneously.

10. The modular patient monitor according to claim 1 wherein said first display autoscales its display of measurements based on at least the number measurements to be displayed.

11. The modular patient monitor according to claim 10 wherein said first display displays measurements larger when fewer measurements are displayed.

12. The modular patient monitor according to claim 1 wherein said first display is rotatable and orients said display of measurements vertically or horizontally according to the rotation.

13. The modular patient monitor according to claim 6 wherein said first display autoscales its display of measurements based on at least the number measurements to be displayed.

14. The modular patient monitor according to claim 13 wherein said first display displays measurements larger when fewer measurements are displayed.

15. The modular patient monitor according to claim 6 wherein said first display is rotatable and orients said display of measurements vertically or horizontally according to the rotation.

* * * * *

UNITED STATES PATENT AND TRADEMARK OFFICE
CERTIFICATE OF CORRECTION

| | | Page 1 of 1 |
|---|---|---|
| PATENT NO. | : 8,840,549 B2 | |
| APPLICATION NO. | : 11/903746 | |
| DATED | : September 23, 2014 | |
| INVENTOR(S) | : Ammar Al-Ali | |

It is certified that error appears in the above-identified patent and that said Letters Patent is hereby corrected as shown below:

On The Title Page (Item 57, Abstract) at line 13, Change "docket" to --docked--.

In The Specification

In column 4 at line 3, Change "Radical" to --Radical®--.

In column 4 at line 8, Change "U.S. Pat. No. _____" to --U.S. App. No. 11/904,046--.

In The Claims

In column 8 at line 65, In Claim 1, after "docking" insert --port--.

Signed and Sealed this
Twenty-second Day of September, 2015

Michelle K. Lee
*Director of the United States Patent and Trademark Office*